US010648957B2

(12) United States Patent
Khusid et al.

(10) Patent No.: US 10,648,957 B2
(45) Date of Patent: May 12, 2020

(54) METHOD AND DEVICE FOR TESTING THE EFFECTIVENESS OF MAGNETIC TREATMENT OF FEED WATER FOR REDUCING MINERAL SCALING IN REVERSE OSMOSIS PROCESSES

(71) Applicants: New Jersey Institute of Technology, Newark, NJ (US); Government of the United States of America, as Represented by The U.S. Department of Interior, The Bureau of Reclamation, Denver, CO (US)

(72) Inventors: Boris Khusid, New Providence, NJ (US); Katherine L. Guerra, Golden, CO (US); Frank Leitz, Evergreen, CO (US); Yueyang Shen, Ithaca, NY (US); Ezinwa O. Elele, Newark, NJ (US); Qian Lei, Newark, NJ (US)

(73) Assignees: Government of the United States of America, The Bureau of Reclamation, Denver, CO (US); New Jersey Institute of Technology, Newark, NJ (US)

( * ) Notice: Subject to any disclaimer, the term of this patent is extended or adjusted under 35 U.S.C. 154(b) by 217 days.

(21) Appl. No.: 15/851,776

(22) Filed: Dec. 22, 2017

(65) Prior Publication Data
US 2018/0180581 A1 Jun. 28, 2018

Related U.S. Application Data

(60) Provisional application No. 62/437,939, filed on Dec. 22, 2016.

(51) Int. Cl.
*G01N 31/02* (2006.01)
*G01N 33/18* (2006.01)
(Continued)

(52) U.S. Cl.
CPC ............ *G01N 31/02* (2013.01); *B01D 61/10* (2013.01); *C02F 1/008* (2013.01); *C02F 1/441* (2013.01); *C02F 1/484* (2013.01); *G01N 15/0606* (2013.01); *G01N 15/0612* (2013.01); *G01N 15/0618* (2013.01); *G01N 15/0625* (2013.01); *G01N 15/0656* (2013.01);
(Continued)

(58) Field of Classification Search
CPC ............... G01N 31/02; G01N 15/0606; G01N 15/0612; G01N 15/0618; G01N 15/0625; G01N 15/0656; G01N 15/0687; C02F 1/441; C02F 1/48–485
See application file for complete search history.

(56) References Cited

PUBLICATIONS

Marshall, et al., Thermodynamics of calcium sulfate dihydrate in aqueous sodium chloride solutions, 0-110°, J. Phys. Chem. 70(12) (1966) 4015-4027.

(Continued)

*Primary Examiner* — Paul M. West
(74) *Attorney, Agent, or Firm* — McCarter & English, LLP

(57) ABSTRACT

A benchtop device flow setup for determining the effectiveness of magnetic treatment of feed water for reducing mineral scaling includes two similar branches, both equipped with a reverse osmosis membrane and a pump that operate in the transient regime at the same flow rate and transmembrane pressure. The flow setup is further fed with a solution at the same level of supersaturation measured in a stirred reactor, however, only one branch exposes the feed to a magnetic field.

10 Claims, 8 Drawing Sheets

(51) Int. Cl.
| | |
|---|---|
| C02F 1/48 | (2006.01) |
| C02F 1/44 | (2006.01) |
| B01D 61/10 | (2006.01) |
| C02F 1/00 | (2006.01) |
| G01N 15/06 | (2006.01) |
| B01D 61/02 | (2006.01) |

(52) U.S. Cl.
CPC ........... *G01N 33/18* (2013.01); *B01D 61/025* (2013.01); *B01D 2311/04* (2013.01); *B01D 2311/24* (2013.01); *B01D 2311/243* (2013.01); *B01D 2311/246* (2013.01); *B01D 2311/2607* (2013.01); *B01D 2311/2642* (2013.01); *C02F 1/481* (2013.01); *C02F 2209/001* (2013.01); *C02F 2209/05* (2013.01); *C02F 2209/11* (2013.01); *C02F 2303/22* (2013.01)

(56) References Cited

PUBLICATIONS

Sohnel, et al., Interpretation of Crystallization Induction Periods, Journal of Colloid Interface Science, 123, 43-50, (1988).
Raju, et al., The Thermodynamics of "scale" Mineral Solubilities. 3. Calcium Sulfate in Aqueous NaCl, Journal of Chemical Engineering, Data 35, 361-367, (1990).
Mulder, Basic Principles of Membrane Technology, Table of Contents and VII Polarisation Phenomena and Membrane Fouling, Kluwer Academic Publishers, Dordrecht, NL, 1991.
He, et al., The seeded growth of calcium sulfate dehydrate crystals in NaCl solutions up to 6 m and 90° C., J. Colloid Interface Sci. 163 (1994) 372-378.
Al-Qahtani, Effect of magnetic treatment on Gulf seawater, Desalination 107 (1996) 75-81.
Baker, et al., Magnetic amelioration of scale formation (review), Water Res. 30, 247-260, (1996).
Baker, S.J. et al., Antiscale Magnetic Pretreatment of Reverse Osmosis Feedwater, Desalination 110 (1997) 151-166.
Colic, et al., The Elusive Mechanism of the Magnetic 'Memory' of Water, Colloid Surface a 154 (1999) 167-174.
Klepetsanis, et al., Role of temperature in the spontaneous precipitation of calcium sulfate dehydrate, Langmuir 15 (1999) 1534-1540.
Lancia, et al., Measuring induction period for calcium sulfate dihydrate precipitation, AIChE J. 45(2) (1999) 390-397.
Wu, et al., Determination of interfacial tension from crystallization and dissolution data: a comparison with other methods. Adv. Colloid Interface Sci. 79 (1999) 229-279.
Lee, et al., Effect of operating conditions on $CaSO_4$ scale formation mechanism in nanofiltration for water softening, Water Res. 34 (2000) 3854-3866.
Fatu, Kinetics of gypsum dehydration, J. Therm. Anal. Calorim. 65 (2001) 213-220.
Hina, et al., Surface induced constant composition crystal growth kinetics studies, The brushite-gypsum system, J. Cryst. Growth 223 (2001) 213-224.
Mullin, Crystallization, 4th Ed., Elsevier, 2001.
Prisciandaro, et al., Gypsum nucleation into sodium chloride solutions, AIChE J. 47(4) (2001) 929-934.
Vedavyasan, et al., Potential use of magnetic fields a perspective, Desalination 134 (2001) 105-108.
Follner, et al., On the real structure of gypsum crystals, Cryst. Res. Technol. 37 (2-3) (2002) 207-218.
Alimi, et al., Kinetics of the precipitation of calcium sulfate dehydrate in a desalination unit, Desalination 157 (2003) 9-16.
Hasson, et al., Induction times induced in an RO system by antiscalants delaying $CaSO_4$ precipitation, Desalination 157 (1-3) (2003) 193-207.
Prisciandaro, et al., The retarding effect of citric acid on calcium sulfate nucleation kinetics, Ind. Eng. Chem. Res. 42 (2003) 6647-6652.
Sheikholeslami, et al., Kinetics and thermodynamics of calcium carbonate and calcium sulfate at salinities up to 1.5 M, Desalination 157 (2003) 217-234.
Mahmoud, et al., Crystal modification of calcium sulfate dihydrate in the presence of some surface-active agents. J. Colloid Interface Sci. 270 (2004) 99-105.
Shih, et al., Morphometric characterization of calcium sulfate dihydrate (gypsum) scale on reverse osmosis membranes. J. Memb. Sci. 252 (2005) 253-263.
Vallee, et al., Effects of pulsed low-frequency electromagnetic fields on water characterized by light scattering techniques: Role of bubbles, Langmuir 21 (2005) 2293-2299.
Kney, et al., A spectrophotometer-based study of magnetic water treatment: Assessment of ionic vs. surface mechanisms, Water Res. 40 (2006) 517-524.
Otsuka, et al., Does magnetic treatment of water change its properties? J. Phys. Chem. B 110 (2006) 1509-1512.
Rahardianto, et al., Diagnostic characterization of gypsum scale formation and control in RO membrane desalination of brackish water. J. Memb. Sci. 279 (2006) 655-668.
Holysz, et al., Effects of a static magnetic field on water and electrolyte solutions, J. Colloid Interface Sci. 316 (2007) 996-1002.
Li, et al., Quantitative study of the effect of electromagnetic field on scale deposition on nanofiltration membranes via UTDR, Water Res. 41 (2007) 4595-4610.
Shannon, et al., Science and technology for water purification in the coming decades, Nature 452 (2008) 301-310.
Uchymiak, et al., Kinetics of gypsum crystal growth on a reverse osmosis membrane, J. Memb. Sci. 314 (2008) 163-172.
Vashisth, et al., K.D.P., Nigam, A review on the potential applications of curved geometries in process industry, Ind. Eng. Chem. Res. 47 (2008) 3291-3337.
Stuyven, et al., Natural suspended particle fragmentation in magnetic scale prevention device, Chem. Eng. Sci. 64 (2009) 1904-1906.
Ambashtaa, et al., Water purification using magnetic assistance: A review, J. Hazard. Mater. 180 (2010) 38-49.
Elimelech, et al., The future of seawater desalination: Energy, technology, and the environment, Science 333 (2011) 712-717.
Gryta, The influence of magnetic water treatment on $CaCO_3$ scale formation in membrane distillation process, Sep. Purif. Technol. 80 (2011) 293-299.
Malaeb, et al., Reverse osmosis technology for water treatment: State of the art review, Desalination 267 (2011) 1-8.
Szczes, et al., Effects of static magnetic field on electrolyte solutions under kinetic condition, J. Phys. Chem. A 115 (2011) 5449-5452.
Lopez-Beceiro, et al., Study of gypsum by PDSC, J. Therm. Anal. Calorim. 109 (2012) 1177-1183.
Vardanega, et al., Effect of magnetic field on the ultrafiltration of bovine serum albumin, Bioprocess Biosyst. Eng. 36 (2013) 1087-1093.
Zaidi, et al., Magnetic field application and its potential in water and wastewater treatment systems, Sep. Purif. Rev. 43 (2014) 206-240.
Shenvi, et al., A review on RO membrane technology: Developments and challenges, Desalination 368 (2015) 10-26.
U.S. Appl. No. 61/635,725, filed Apr. 19, 2012.

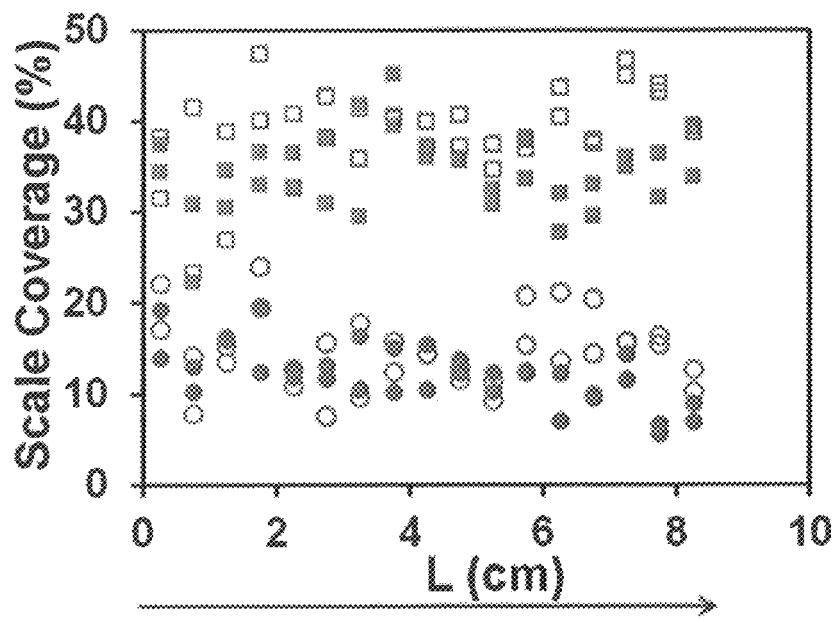
FIG. 5A
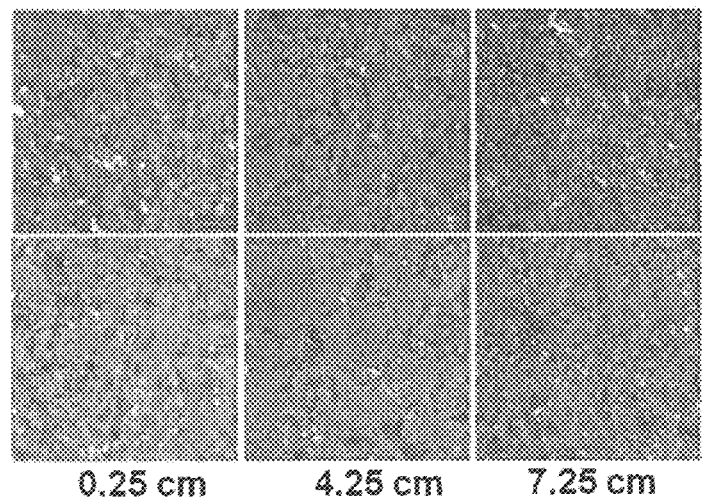
FIG. 5B
FIG. 5C

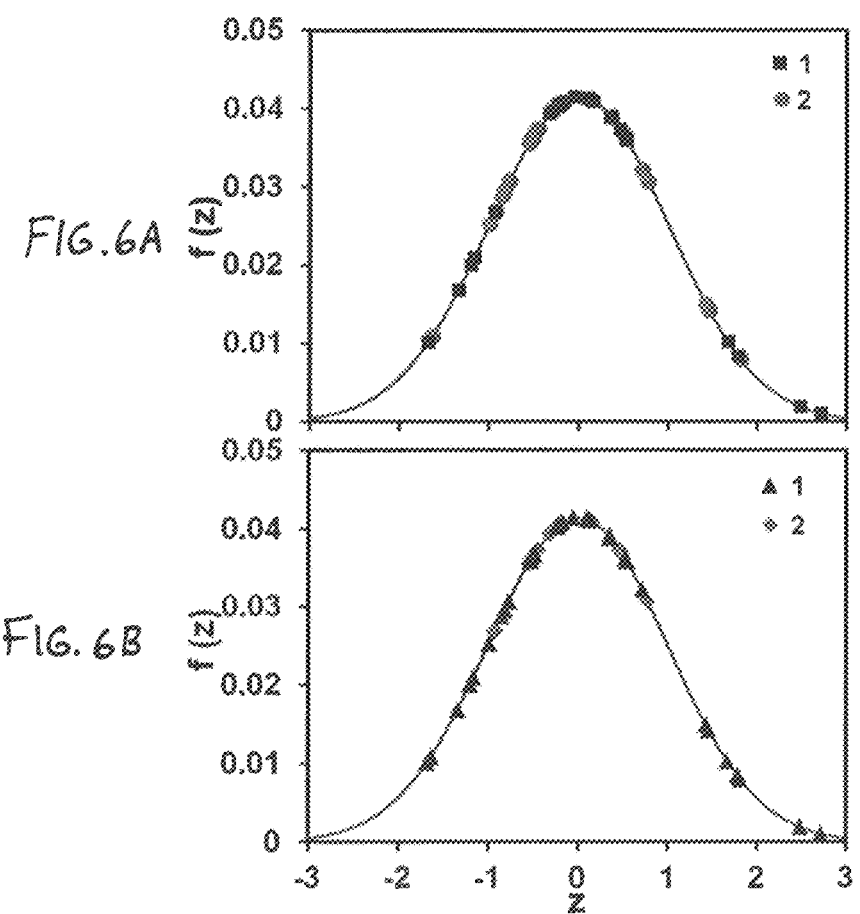

METHOD AND DEVICE FOR TESTING THE EFFECTIVENESS OF MAGNETIC TREATMENT OF FEED WATER FOR REDUCING MINERAL SCALING IN REVERSE OSMOSIS PROCESSES

CROSS-REFERENCE TO RELATED APPLICATIONS

The present application claims priority benefit to U.S. Provisional Patent Application No. 62/437,939, entitled "Method and Device for Testing the Effectiveness of Magnetic Treatment of Feed Water for Reducing Mineral Scaling in Reverse Osmosis Processes," which was filed on Dec. 22, 2016. The content of the foregoing provisional application is hereby incorporated by reference.

GOVERNMENT FUNDING

This invention was made with government support under IIP 1034710 awarded by the National Science Foundation Industry/University Cooperative Research Center for Membrane Science, Engineering and Technology Center. The government has certain rights in the invention.

BACKGROUND

1. Technical Field

The present disclosure is directed to a methodology and device/system for quick (e.g., 10-30 min) benchtop tests of the effectiveness of magnetic treatment of feed water for reducing mineral scaling on a reverse osmosis (RO) membrane.

2. Background Art

Water shortage is one of the most urgent global challenges in the 21st century. The population growth and shifting, industrialization, contamination of available freshwater resources, and climate change exacerbate water shortages and safety in various arid and even high-rainfall regions worldwide. The needs to meet greater societal future demands and ecological benefits have long motivated research and developments for a solution to water scarcities. The only methods incorporated successfully to provide additional fresh water production beyond what is available from the hydrological cycle are the desalination and water reuse. Although costs of water reuse from rivers and groundwater, recycled water, and water conservation are lower than those of desalinated water, these portable water sources are not always available, whereas desalination offers a seemingly unlimited, steady supply of high-quality water, without impairing natural freshwater ecosystems.

Desalination is the process of removing salt from seawater or brackish water to produce fresh water. Reverse osmosis (RO) is the major membrane-based technology for desalination because of its efficiency. It is a pressure-driven process in which an applied pressure is used to overcome the osmotic pressure whereby a semi-permeable membrane lets solvents pass through but rejects ions in the feed water. RO has emerged as the leader in future desalination installations due to a smaller amount of energy consumption that is several times smaller than that of other technologies. RO is considered to be the key to increasing water supplies for drinking water production worldwide [1].

RO systems for production of drinking water from seawater and saline aquifers has advanced significantly in the past decade, owing to the development of more robust membranes and efficient energy recovery methods [1-4]. However, membrane fouling remains among the major RO challenges. Sparingly soluble salts in feed water can crystallize directly onto the RO membrane surface, forming an adherent mineral scale that causes the permeate flux to decline and eventually damages the membrane.

The most widespread strategy employed to reduce membrane fouling is the use of antiscalant additives to the feed water that can inhibit the nucleation and growth of scale deposits. However, chemical cleaning is not free from hazards and facilitates metallic corrosion and biofouling by microorganism colonies. Moreover, chemical treatments are highly specific to a particular composition of the feed water with respect to their effectiveness and may substantially affect the composition of drinking water. Environmental and regulatory agencies frequently object to disposal of antiscalant and biocidal chemicals present in concentrate (marine, brackish, wastewater). These chemicals also complicate beneficial product recovery and increase operating costs of RO desalting.

There are a host of currently-marketed technologies which use combinations of magnetic, electrostatic, and electromagnetic fields for treatment of feed water. These technologies are compelling due to their simplicity and relatively low cost. Magnetic and/or electrical-based conditioners of feed water are available in a wide variety of configurations, and can be plumbed in or clamped on. They are sold worldwide and claimed to suppress scale formation, increase membrane lifetime, and replace feed treatment with chemicals.

A majority of marketed devices use magnetic water treatment employing an array of permanent magnets or electromagnets. The history of magnetic water treatment in various applications is long and controversial, marked by claims for and against their effectiveness.

Most studies published in the open literature reviewed in Refs. [5]-[7] are focused on testing of anti-scale magnetic treatment of water in heating systems and RO and nanofiltration processes for producing drinking water. While many publications claimed no significant effects of magnetic treatment, many publications considered to be sufficiently credible demonstrated that the magnetic treatment facilitated reduction of scale deposition or removal of scale or appearance of softened deposits that were easier to remove. Furthermore, the treatment influence was reported to last up to hundreds hours after a field had ceased. Benefits of magnetic treatment were found to depend strongly on various operating parameters, such as field strength and direction with respect to the flow, exposure time, temperature, channel geometry and flow rate, water composition, and pH level. Several hypotheses are typically invoked to explain the efficiency of magnetic treatment of water in the technical literature [8-20]. It is usually agreed that magnetic treatment facilitates bulk precipitation of sparingly soluble salts in feed water, thereby suppressing formation of a tightly adherent scale layer.

Given the widespread availability of inexpensive magnetic and electrical based water conditioners advertised for replacement of chemical treatment of water, it is expected that such devices will continue to draw interest across the industry to explore whether they are efficient in a particular RO system. Due to the high costs of tests on large RO units, it is an urgent need to develop a benchtop test for evaluating whether a particular electro-magnetic treatment can be useful under specific operating conditions of a large industrial RO system and further large-scale testing effort of this technique is warranted.

The present disclosure presents an advantageous method and benchtop device for quickly testing the effectiveness of a water conditioner that is claimed to improve the lifetime efficiency of a large industrial RO system. These and other needs are addressed by the methods and devices/systems of the present disclosure.

SUMMARY

The present disclosure provides a method and a benchtop device/system for the quick evaluation of the effectiveness of an electro-magnetic water conditioner to improve the lifetime efficiency of a large industrial RO system by reducing mineral scaling on a reverse osmosis membrane in the flow system of interest.

The disclosed method generally includes two steps: (1) quantification of the degree of feed water supersaturation by measuring the kinetics of precipitation of a sparingly soluble salt in a stirred reactor and (2) simultaneous measurements of the scale coverage over the membrane in the transient regime of crossflow filtration in the provided benchtop device operating in the single-pass flow mode for treated and not treated feed water over the same period of time at the same transmembrane pressure, the same flowrate, and the same desired degree of water supersaturation that is the main factor governing the scale formation. In the transient regime of crossflow filtration that occurs before the concentration polarization forms, variation along the flow pathway of the degree of water supersaturation with a sparingly soluble salt near the membrane surface is negligible that enables one to choose and control it. As mineral scale forms in regions where salt gradually accumulates during hundreds of hours of operation, it usually occurs in regions of a spiral-wound RO membrane module which are adjacent to spacers due to a low cross flow velocity. Therefore to evaluate whether passing the feed water through a tested magnetic and/or electric water softener could reduce scale formation in regions of a sufficiently high salt supersaturation, quick tests are carried out on a feed water having a high degree of supersaturation at a relatively low flow rate.

The solution supersaturation is quantified in step 1 by measuring one of the feed characteristics (e.g., electrical conductivity, turbidity, amount of precipitates, etc.) in a stirred reactor during a certain period of time to find the total relative change of this parameter from the beginning to the end of the precipitation process. The main aspect of the presented method in step 2 is that testing is conducted in the transient regime of crossflow filtration (explained below) that enables one to (i) use a much higher degree of supersaturation of feed water than in conventional tests and (ii) control it as variations of the solute concentration near the membrane surface along the flow pathway in the transient regime are insignificant. Therefore, a much shorter testing time is required in step 2 for measurements of the scale coverage formed on the membrane surface, in treated and not treated feed water, to accumulate statistically significant data for evaluation of the effectiveness of the tested water conditioner to reduce the scale formation over the range of variations in the degree of feed water supersaturation under specific operating conditions of the large flow system of interest for which the range of variations in the degree of water supersaturation along the flow pathway is quantified by using the data acquired in step 1.

Conventional flow tests are conducted under significant variations of the solution composition along the flow pathway (referred to in the relevant literature as concentration polarization) that makes it difficult to use measurements of scale deposits in these tests for prediction whether the electro-magnetic treatment of feed water in a water conditioner can improve the lifetime efficiency of a large industrial system. Specifically, the degree of solution supersaturation in a benchtop device in these tests cannot be controlled and thereby compared to the degree of solution supersaturation in a large industrial system. Contrary to conventional practice, scale deposition in the proposed method and device is measured in step 2 in a transient regime (i.e., before concentration polarization forms) at a controlled level of supersaturation of a sparingly soluble salt whose variation along the flow pathway in the benchtop unit is insignificant. This approach enables one to quantify and control physical and chemical characteristics which can affect the mineral scale formation but cannot be controlled in conventional tests. To improve the test resolution in step 2, the flow device includes two similar branches, each equipped with identical residence time coils, pumps and RO units. The branches are operated in parallel in a single-pass mode of flow through the RO unit at the same flow rate and transmembrane pressure and fed with a solution at the same level of supersaturation, but the feed is exposed to a treatment only in one of them.

Variation of the solute concentration along the flow pathway in crossflow filtration is known to be controlled by convection and diffusion of the solute. Conventional benchtop tests are carried out under conditions of the fully developed mass boundary layer for which the solute transport by convection along and by diffusion across the flow pathway dominate. Under these testing conditions, the solute concentration near the membrane surface varies along the flow pathway. In contrast, the proposed quick testing methodology employs the transient regime of the solute transport in step 2 before the concentration polarization forms, i.e., while the convection and diffusion across the flow pathway dominate but the contribution of the solute convection and diffusion along the flow pathway is insignificant. Accordingly, variation of the solute concentration near the membrane surface along the flow pathway in the proposed testing device is insignificant. Implementation of the proposed testing method is described below. The proposed method for quick benchtop screening will also be useful to evaluate the effectiveness of other technologies for water treatment in a wide range of flow systems.

In exemplary embodiments, steps 1 and 2 of the disclosed testing methodology have been validated by conducting experiments to investigate the effects of magnetic treatment on gypsum deposition in a flow through a benchtop RO system. Polarized microscopy with image processing software, scanning electron microscopy (SEM), X-ray diffractometry (XRD), and differential scanning calorimetry (DSC) were used to characterize the gypsum scale formed on RO membranes. Testing was carried out in a single-pass flow through an RO unit of an aqueous $CaSO_4/NaCl$ solution at controlled supersaturation with $CaSO_4$ that was quantified by using data on the kinetics of precipitation of gypsum in a stirred reactor. The flow setup includes two similar branches, both equipped with an RO unit and a pump, that are operating in the transient regime at the same flow rate and transmembrane pressure, and fed with a solution at the same level of supersaturation, but only one feed was exposed to a magnetic field.

The disclosed methodology and devices/systems have wide-ranging applicability in supporting/facilitating quick benchtop tests across water treatment technologies, e.g., for evaluating the efficiency of a range of technologies for water treatment in flow systems by providing tests to evaluate the efficiency of a particular water softener under specific operating conditions of a large industrial RO system.

Additional features, functions and benefits of the present disclosure will be apparent from the detailed description which follows, particularly when read in conjunction with the appended figures.

BRIEF DESCRIPTION OF THE FIGURES

To assist those of skill in the art in making/using the disclosed methods, devices and systems, reference is made to the accompanying figures, wherein:

FIG. 5A shows a plot related to washed and not washed RO membranes tested according to the present disclosure;

FIGS. 5B and 5C show images related to washed and not washed RO membranes tested according to the present disclosure;

FIGS. 6A and 6B are plots showing scale deposit percentages according to the present disclosure;

DESCRIPTION OF EXEMPLARY EMBODIMENT(S)

Figure 1:
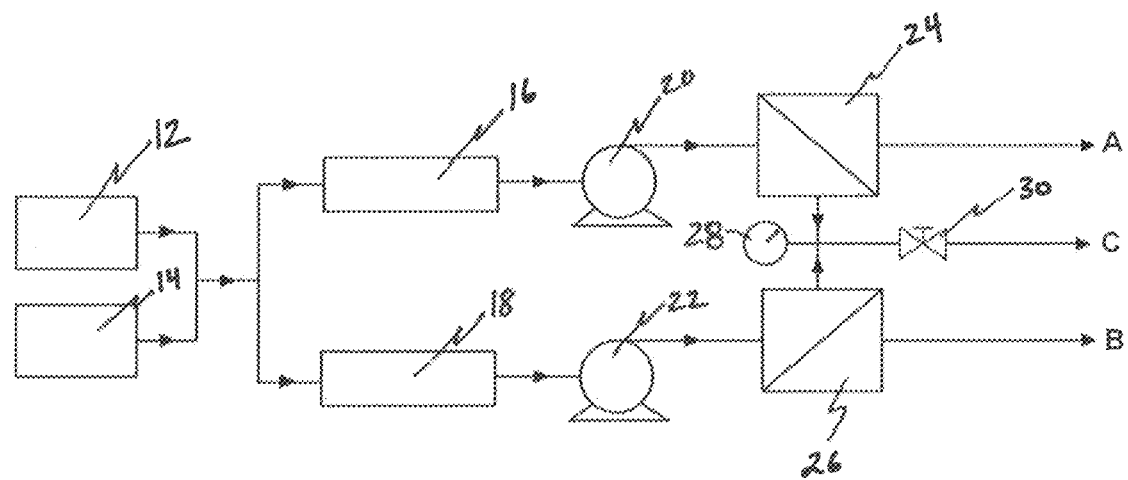
FIG. 1 is a schematic of an exemplary flow diagram according to the present disclosure.

The present disclosure is directed to a methodology and device/system that supports, inter alia, quick (e.g., 10-30 min) benchtop tests of the effectiveness of electro-magnetic treatment of feed water for reducing mineral scaling on a reverse osmosis (RO) membrane. Exemplary implementations and applications of the disclosed methods/devices/systems for testing a magnetic water conditioner are described herein. However, the present disclosure is not limited by or to the exemplary implementations and/or applications described herein, but instead may take various forms and be employed in wide-ranging applications, as will be readily apparent to persons skilled in the art based on the description provided herein.

The disclosed method generally includes two steps: (1) quantification of the degree of feed water supersaturation by measuring the kinetics of precipitation of a sparingly soluble salt in a stirred reactor and (2) simultaneous measurements of the scale coverage over the membrane in the transient regime of crossflow filtration for treated and not treated feed water in the provided benchtop device over the same fixed period of time at the same fixed pressure, the same fixed flowrate, and the same fixed degree of supersaturation under conditions that the variation of the degree of water supersaturation near the membrane surface along the flow pathway in the provided benchtop device is insignificant.

1. Testing Methodology

Scale forms on a membrane when the amount of a sparingly soluble salt in water flowing in an RO system exceeds the salt solubility. A high supersaturation of a solute in a layer at the membrane surface along the flow pathway is gradually built in large industrial RO systems due to transfer of water through the RO membrane (referred to as concentration polarization) [21]. Due to low solution supersaturation of feed solution in conventional tests that are conducted in the presence of concentration polarization in a benchtop device, scale deposition on a membrane is measured with control of the flow rate, pressure, and temperature to form a sufficiently large scale coverage of the membrane but without control of the degree of solution supersaturation as it varies along the flow pathway. Efficiency of water treatment is estimated by comparing measurements in two benchtop tests, one operating on untreated feed water and the other on feed water that passes through the electric and/or magnetic field(s). Due to the small size of a benchtop RO unit, measurements of scale deposits formed in these tests, during a relatively short exposure time, are undesirably close in value. As the degree of solution supersaturation is not controlled in these tests, it is difficult to use the acquired data for prediction whether the electric and/or magnetic treatment device would improve the lifetime efficiency of a large industrial plant where the variation of the water composition and, accordingly, the degree of solution along the flow path through a large RO system is different from that in the benchtop test device.

Figure 2:
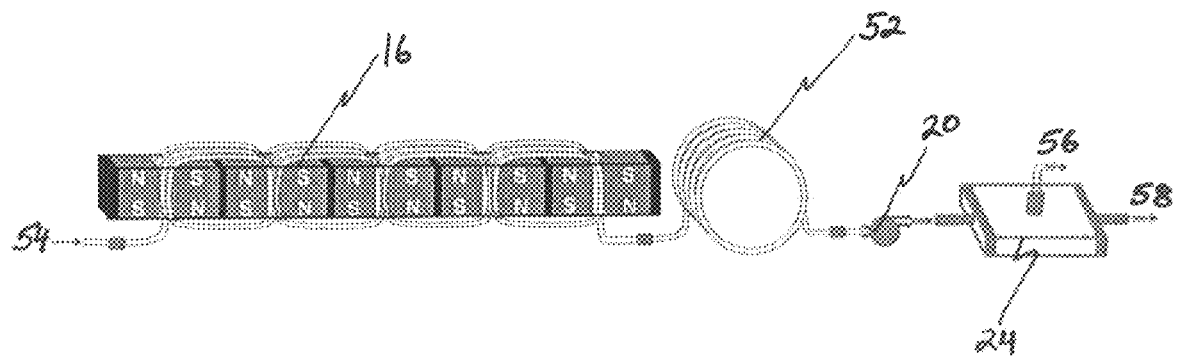
FIG. 2 is a schematic of an exemplary flow assembly according to the present disclosure.

The disclosed methodology is based on a certain analogy between precipitation processes in a stirred reactor and in a flow system since as initial nuclei are formed, processes of crystal growth are then controlled by similar mechanisms in the surrounding supersaturated solution [22]. A simple way to characterize the precipitation kinetics in a supersaturated solution is to record changes with time in a stirred vessel of the electrical conductivity, or the intensity of scattered and transmitted light, or the concentration of specific ions (e.g., $Ca^{2+}$ ions for gypsum), or the amount of precipitates, or other parameter(s) in the course of precipitation. The solution supersaturation is then characterized by the value of $\xi(t)$ that is the ratio between a change in one of such characteristics during a period of time t and the total change so that $\xi=0$ and $\xi=1$ are at the beginning and the end of the precipitation process, respectively. Therefore, step 1 in the disclosed experimental test was to measure the kinetics of precipitation from a supersaturated solution in a stirred reactor by recording changes of the feed characteristics, e.g., electrical conductivity, turbidity, and the concentration of $Ca^{2+}$ ions, as demonstrated in FIG. 4. In step 2, scale formation was measured in a flow device at a certain value of $\xi$ in the feed solution under the controlled flow rate Q and transmembrane pressure P in an RO unit (FIGS. 1 and 2). The value of $\xi$ was determined by comparison of the solution electrical conductivity measured at the RO unit inlet and outlet to data on the time variation of the solution $\xi$ in the stirred reactor.

Experiments in step 2 were carried out in a single-pass mode of flow through the RO unit to control the degree of solution supersaturation for an extended period of time. Compared to conventional testing, often conducted in a close-loop recirculation mode needed to form a sufficiently large scale layer on the membrane, the single-pass flow regime is also better suited to mimic the single-pass operation of industrial RO systems. To measure scale formation for a fixed value of the degree of solute supersaturation at the membrane surface of industrial RO systems, experiments may be conducted in the above-mentioned transient regime of crossflow filtration (i.e., before the concentration polarization formed) for which variations of the solute concentration near the membrane surface along the flow pathway are insignificant so that the degree of solute supersaturation $\xi$ in the benchtop device is specified by the composition of a feed solution prepared for the test.

Under operative experimental conditions, changes in the average percentage of membrane surface area covered with scale deposits, along and across the flow, are statistically insignificant, as demonstrated in FIGS. 6 and 7. To improve resolution of the magnetic treatment effects, a differential scheme was adopted by using two similar branches operating in parallel at the same flow rate and transmembrane pressure and fed with a supersaturated solution at the same value of $\xi$ (FIG. 1). Each branch included a pump and an RO unit. One valve was used to regulate flows in both branches. One of these RO units received the solution that passed through the magnetic field, whereas the other received the solution that passed through a similar flow assembly (referred to as the dummy unit) but was not exposed to the field.

The test configuration and experimental conditions allow direct comparison of scale deposits formed in the treated and untreated supersaturated solution at the same value of $\xi$. The use of parameter $\xi$ that quantifies the supersaturation level of a sparingly soluble salt in feed solution provides an advantageous mechanism for employing benchtop measurements for predicting the efficiency of magnetic treatment of feed water in an industrial RO system.

The disclosed approach for predicting the effectiveness of the tested water conditioner in the system of interest generally involves (1) measuring variations of electrical conductivity or other parameters that characterize solution supersaturation along the flow path through the system to find the range of supersaturation $\xi$ and then (2) conducting tests over the range of $\xi$ values that are determined by comparing measurements within the system of interest to data on the variation of the electrical conductivity or other parameters characterizing supersaturation of feed water that were acquired during precipitation in a stirred reactor in step 1. The feed treatment with a tested water conditioner would be successful only if benchtop tests reveal its efficiency over a range of $\xi$ found in the system of interest.

2. Experimental a. Materials

All experiments were carried out on aqueous solutions of $CaCl_2$, NaCl, and $Na_2SO_4$ at room temperature. ACS grade (>99%) powders of (NaCl), calcium chloride dihydrate ($CaCl_2.2H_2O$) and sodium sulfate ($Na_2SO_4$) were acquired from Sigma-Aldrich (St. Louis, Mo., USA). Stock solutions of $CaCl_2$/NaCl and $Na_2SO_4$/NaCl were prepared by adding appropriate molar amounts of NaCl, $CaCl_2.2H_2O$ and $Na_2SO_4$ to de-ionized (DI) water. A proper amount of a salt powder was weighed on a Mettler Toledo AL204 Laboratory Balance (Mettler Toledo, Columbus, Ohio, USA). Stock solutions were prepared in 5-L tanks, allowed to stand to ensure complete dissolution of salts and were then filtered through a Supor 200 PES Membrane Disc Filter with 0.2 μm pores (Pall, Cortland, N.Y., USA) to remove remaining particulates. An aqueous solution supersaturated with $CaSO_4$ was formed by mixing two stock solutions such that

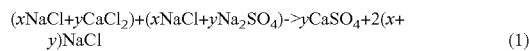

(1)

b. Apparatuses and Procedures i. Stirred Reactor

The precipitation kinetics in a solution supersaturated with $CaSO_4$ was studied in a 1-L cylindrical vessel stirred with a VWR VOS 16 S41 Overhead Stirrer Mixer (VWR, Radnor, Pa., USA) with a two-blade impeller having a diameter of 1.125" at a rotational speed of 427 rpm. The supersaturated mixture was prepared by charging the vessel with 0.4 L of a solution of $CaCl_2$/NaCl and 0.4 L of a solution of $Na_2SO_4$/NaCl. Changes of the mixture electrical conductivity, turbidity, and $Ca^{2+}$ concentration were measured with the relevant sensors submerged under the solution surface: a conductivity meter (CDH-SD1, Omega Engineering, Stamford, Conn., USA), a turbidity probe (OBS-3+ Turbidity Sensor, Campbell Scientific, Logan, Utah, USA), and a $Ca^{2+}$ ion selective electrode (perfectION™ Calcium Combination Electrode, Mettler-Toledo, Columbus, Ohio, USA). Measurements were recorded by a data acquisition system (Labjack U6 Pro, Lakewood, Colo., USA) at 5 Hz.

Once the experiment was completed, particles formed in the vessel were filtered out with a Pall Supor 200 Membrane Disc Filter with 0.2 μm pores and then dried overnight in a desiccator at room temperature.

ii. Flow Setup

The effects of the magnetic treatment of a solution supersaturated with $CaSO_4$ on scale formation on a RO membrane was studied in flow setup 10 which includes two branches, see FIG. 1. A supersaturated solution in both branches was formed by feeding a pump through a T-junction pipe with solutions taken from two 1-L tanks; one filled with a solution of $CaCl_2$/NaCl 12 and the other with a solution of $Na_2SO_4$/NaCl 14. Each branch of setup 10 included a laboratory cross-flow RO unit 24, 26 (Crossflow Cell CF042, Sterlitech, Kent, Wash., USA) with a flat membrane of 42 $cm^2$ active area (3.625"×1.800", slot depth 0.09") and maximum operating pressure and temperature of 1,000 psi and 80° C.; a high performance liquid chromatography (HPLC) dual-head digital pump 20, 22 (LabAlliance Prep 100, Scientific Systems, State College, Pa., USA) equipped with a pressure monitoring unit and a built-in pulse damper to deliver low flow rates with less than 2% RSD pulsations; and an OHAUS Scout Pro balance (OHAUS, Parsippany, N.J., USA) for measuring the weight of permeate collected in a glass beaker that was recorded with a data acquisition system (Logger Pro software, Vernier Technology, Beaverton, Oreg., USA) at frequency of 60 Hz.

The RO unit inlet was connected to the pump outlet with a thin metal tube. The 1-L tank was connected to the pump inlet with the Tygon S3 B-44-3 tubing OD 3/16", ID 1/8" (Saint-Gobain Performance Plastics, Wayne, N.J., USA). The degree of solution supersaturation in the RO unit was computed from data on its electrical conductivity measured at the unit inlet and outlet. Retentate exits of both RO units were connected to an ultra-precision needle valve 30 (up to 3,000 psi, McMaster Carr, Robbinsville, N.J., USA) to regulate simultaneously pressure in both branches. The pressure was monitored with a high-pressure Swagelok gauge 28 (0-1,500 psi with stainless tube and connectors, Mountainside, N.J., USA). One branch of the setup was equipped with five of commercially available magnetic water softeners 16, i.e., magnetic treatment units, arranged in series. An example of a magnetic treatment unit is Model MSW 4, Applied Magnets, Plano, Tex. It will be understood that other suitable magnetic treatment units could be employed.

Each water softener includes two parallel 2"×1"×1" neodymium magnets spaced at a distance of 1 cm apart using two stainless steel studs as guides. About 20 ft of Tygon tubing was wrapped around the magnets in 24 coils. The field strength of 8,000 G in the gap between magnets was measured with a DC Gaussmeter (Model 1-ST, AlphaLAB Inc., Salt Lake City, Utah, USA). The other branch was equipped with a dummy unit 18 that was fabricated from wooden blocks and had the same arrangement of 20-ft coiled tubing as in the magnetic treatment unit 16. The tubing in the magnetic unit 16 and dummy unit 18 was connected to the pump inlet either directly or through additional 100-ft tubing 52, see FIG. 2, to change the degree of solution supersaturation in the RO unit by increasing its residence time in the flow assembly. With specific reference to a schematic flow assembly 50 of FIG. 2, feed water 54 is fed through magnetic unit 16 and through additional 100-ft tubing 52 into pump 20. Attached to the outlet of pump 20 is cross-flow RO unit 24 which includes two outlets—permeate 56 and retentate 58.

Rolls of flat-sheet polyamide membranes Dow Filmtec BW30 were stored in a container with water placed in a refrigerator. Specimens for flow experiments were prepared using a punch and die set provided by Sterlitech. The specimens were then rinsed with DI water and mounted in RO units. DI water at a flow rate of 5-10 mL/min was used to clean the flow setup for at least 30 min before and after each experimental run. A supersaturated solution was introduced in the setup to replace water at a flow rate of 5 mL/min. As water was replaced, the solution flow rate was gradually increased to a desired value. Once the flow stabilized, the pressure in the setup was gradually increased to 800 psig by closing the needle valve 30. Recording of the collected amount of permeate began as its consistent flow was observed. Tests were carried out for about 10-30 min at fixed flow rates (Q=10, 15, 20, and 25 mL/min) of a supersaturated solution. As the HPLC pump 20, 22 maintained a constant flow rate by increasing the pressure, the test was stopped earlier if the pump pressure accidentally exceeded 900 psig due to clogging.

The main parameters of the flow regimes used in tests are listed in Table 1, shown below, wherein: the average flow velocities in the tubing, $u_T$, and in the RO unit, $u_{RO}$; the corresponding Reynolds numbers $Re_T = u_T d_T / v$ and $Re_{RO} = u_{RO} h_{RO} / v$, where $d_T$ is the tubing diameter, $h_{RO}$ is the slot depth of the RO unit and $v=1$ cSt is the water kinematic viscosity; the residence time in 20-ft coiled tubing arranged in the magnetic and dummy units (items 3 and 4 in FIG. 1 and item 1 in FIG. 2), $t_{20\,ft} = L_1/u_T$ with $L_1=20$ ft; the residence time in the 100-ft coiled tubing (item 2 in FIG. 2), $t_{100\,ft} = L_2/u_T$ with $L_2=100$ ft; the total residence time in 120-ft coiled tubing when both coils were used, $t_{120\,ft} = t_{20\,ft} + t_{100\,ft}$; the residence time in the RO unit, $t_{RO} = L_{RO}/u_{RO}$ with $L_{RO}=3.625"$.

$\sqrt{d_T/2R}$ where $d_T$ is the tube diameter and R is the radius of curvature of the tube centerline. The radii of curvature of 20-ft coiled tubing 16, 18 and 100-ft coiled tubing 52 are $R_{20\,ft}=1.42"$ and $R_{100\,ft}=2.76"$, respectively. The values of Dean numbers calculated for these coils, $De_{20\,ft}$ and $De_{100\,ft}$, are listed in Table 1. The vortices arising in these coiled tubing are known to provide an effective means for mixing in a flowing fluid [23].

Once the test was completed, tested membranes were taken out of the RO units 24, 26, gently dipped in DI water 10 times to remove loosely bound particles from the membrane that were most likely formed near the membrane surface, dried for 1 day in a desiccator at room temperature, and then stored dry in a desiccator for further analysis. For comparison, a number of tested membranes were dried in a desiccator without rinsing in DI water.

c. Optical Microscopy

Figure 3:
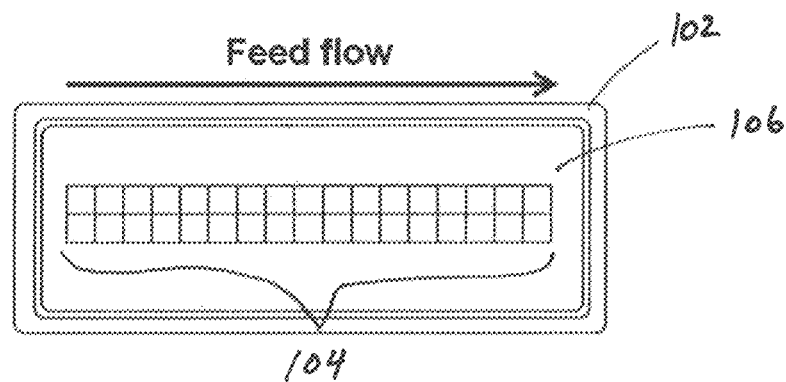
FIG. 3 is a schematic of a grid of squares drawn across the central part of a membrane surface according to the present disclosure.

An optical microscope (Nikon SMZ1500, Melville, N.Y.) with 1× objective at 4× magnification was used to study the scale deposits formed on tested membranes. The objective was fitted with the polarizer and analyzer to improve the observation of the scale pattern. To measure the area of a membrane 102 covered by scale deposits, a grid of 5 mm×5 mm squares 104 was drawn across the central part of the membrane surface 106, seventeen in the flow direction and two in the perpendicular direction, see FIG. 3. An image of each grid cell was recorded with a high-resolution CoolSNAP HQ 2 CCD camera (Photometrics, Tucson, Ariz., USA). NIS Advanced Imaging software (Nikon Instruments, Melville, N.Y., USA) and ImageJ (the public domain image-processing software developed at the National Institute of Health, USA) was used to compute the percentage of area covered with scale deposits in a grid cell.

d. Scanning Electron Microscopy (SEM)

A field emission scanning electron microscope (FESEM) LEO1530VP GEMINI (Carl Zeiss, Peabody, Mass., USA) was used to observe the morphology of scale deposits formed on tested membranes. Specimens for analysis were cut out of a tested membrane and coated with carbon using a sputter coater (Bal-Tec MED 020 HR).

e. X-Ray Diffractomerty (XRD)

A PANalytical Empyrean Series 2 X-Ray Diffractometer (Westborough, Mass., USA) equipped with a Cu Kα X-ray source was used to determine the crystallinity of particles precipitated from a solution in the stirred reactor and the scale deposits formed on a tested membrane. An XRD diffraction pattern was recorded in the angular range (2θ) from 5° to 60° with a step-width of 0.013° at a scanning speed of 0.1° per second. The recorded diffraction patterns

TABLE 1

| Q (mL/min) | $u_T$ (cm/s) | $u_{RO}$ (cm/s) | $Re_T$ | $Re_{RO}$ | $De_{20\,ft}$ | $De_{100\,ft}$ | $t_{20\,ft}$ (min) | $t_{100\,ft}$ (min) | $t_{120\,ft}$ (min) | $t_{RO}$ (s) |
|---|---|---|---|---|---|---|---|---|---|---|
| 10 | 2.1 | 0.16 | 67 | 3.6 | 14.0 | 10.1 | 4.8 | 24.1 | 29.0 | 57.7 |
| 15 | 3.2 | 0.24 | 100 | 5.5 | 21.0 | 15.1 | 3.2 | 16.1 | 19.3 | 38.5 |
| 20 | 4.2 | 0.32 | 134 | 7.3 | 28.0 | 20.1 | 2.4 | 12.1 | 14.5 | 28.9 |
| 25 | 5.3 | 0.40 | 167 | 9.1 | 35.0 | 25.2 | 1.9 | 9.7 | 11.6 | 23.1 |

Unlike the flow in a straight tube, the fluid motion in a coiled tube is not parallel to the tube centerline. Centrifugal forces acting outward from the center of curvature of the tube centerline generate a secondary flow in the cross-sectional plane of the tube. The intensity of this secondary flow is characterized by the Dean number [23] De=Re were compared with data on gypsum ($CaSO_4 \cdot 2H_2O$) and anhydrite ($CaSO_4$) in the instrument library.

f. Differential Scanning Calorimetry (DSC)

DSC curves of particles precipitated from a solution in the stirred reactor and collected from the scale deposits on a membrane in a RO unit were recorded on a Mettler Toledo DSC (Columbus, Ohio, USA). The calorimeter was calibrated with a Mettler Toledo indium sample. Measurements were conducted in semi-hermetically sealed aluminum cells on 3-mg specimens heated from room temperature to 250° C. at a rate of 10° C./min.

g. Statistical Analysis of Data

Scale formation on the RO membrane surface from a solution supersaturated with $CaSO_4$ under the experimental conditions of FIG. 1 may be affected by the magnetic treatment of a solution, the solution flow rate, the degree of solution supersaturation $\xi$ in the RO unit, and the distance from the RO unit inlet to a particular location on the surface along the flow path. In the statistical analysis, measurements of scale deposits on tested membranes were arranged in k comparison groups, each affected by a specific factor or the level of this factor. A statistical hypothesis test [24], often referred to as F-test, was then used to determine whether these factors or their levels affected scale formation. The null hypothesis, $H_0$, was that a difference between measurements of the percentage of area covered with scale deposits in a grid cell on the membrane surface, FIG. 3, within a particular group compared with other groups appeared by chance. The alternative hypothesis, $H_1$, was that this difference was influenced by factors under investigation. The test was based on a comparison between the means and variances among scale deposits computed separately for measurements within a specific group and the overall values computed for all the measurements.

The following three-step procedure was used for testing the null hypothesis [24]: (1) compute the mean $\overline{X}_j$ and variance $S_j^2$ for each of k groups as $$\overline{X}_j = \frac{1}{n_j}\sum_{i=1}^{n_j} X_{ij} \text{ and } S_j^2 = \frac{1}{n_j-1}\sum_{i=1}^{n_j}(X_{ij}-\overline{X}_j)^2,$$

where $n_j$ (j=1, ..., k) is the number of measurements in the $j^{th}$ group and $X_{ij}$ (i=1, ..., $n_j$) are measurements in this group; (2) compute the overall mean $\overline{X}$ and variance $S^2$ for all the groups as $$\overline{X} = \frac{1}{N}\sum_{j=1}^{k}\sum_{i=1}^{n_j} X_{ij} \text{ and } S^2 = \frac{1}{N-1}\sum_{j=1}^{k}\sum_{i=1}^{n_j}(X_{ij}-\overline{X})^2,$$

$$\text{where } N = \sum_{j=1}^{k} n_j$$

is total number of measurements; and (3) compute F factor as $F=MS_B/MS_W$ with $$MS_B = \frac{1}{k-1}\sum_{j=1}^{k} n_j(\overline{X}_j - \overline{X})^2 \text{ and} \quad (2)$$

$$MS_W = \frac{1}{N-k}\sum_{j=1}^{k}\sum_{i=1}^{n_j}(X_{ij}-\overline{X}_j)^2,$$

where $MS_B$ characterizes the mean variability between the groups and $MS_W$ characterizes the mean variability within these groups.

The value of F will be large only if the variability between the groups is large compared to the variability within the groups. There are two criteria for rejecting or accepting the null hypothesis, both depend on two degrees of freedom, k−1 and N−k, and the chosen significance level $\alpha$ that yields the confidence level 100·(1−$\alpha$) %, [24]. One of them is to calculate $F_\alpha$ that is a function of $\alpha$ and the degrees of freedom: F should exceed $F_\alpha$ for the null hypothesis to be rejected. The other is to calculate the p-value that is a function of F and the degrees of freedom and find $\alpha$ for rejecting, $\alpha$>p, or accepting, $\alpha$≤p, the null hypothesis.

3. Results and Discussion a. Precipitation Kinetics

Figure 4:
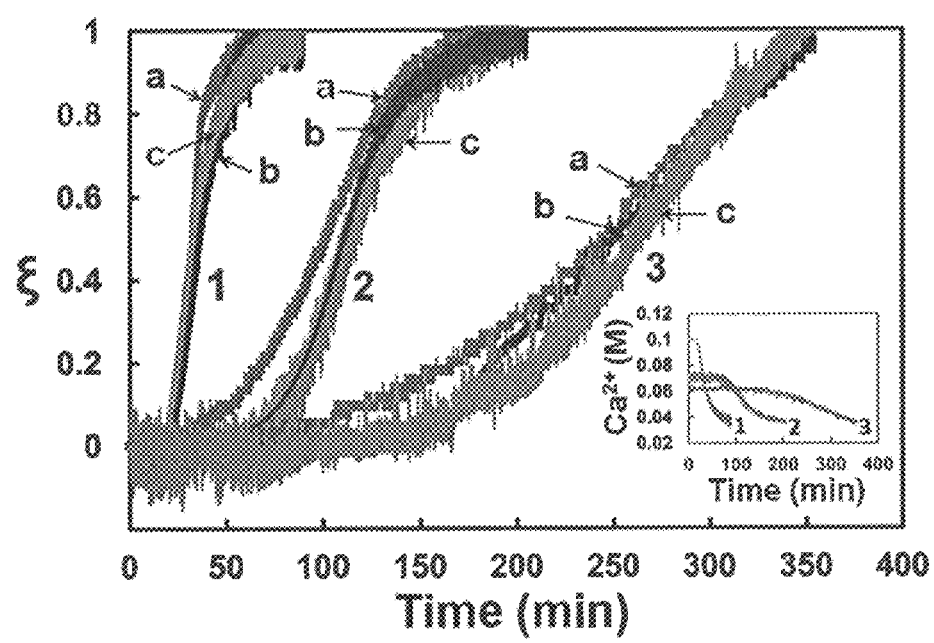
FIG. 4 is a plot showing relative changes in a test solution according to the present disclosure.

With reference to FIG. 4, changes of the electrical conductivity (a), turbidity (b), and $Ca^{2+}$ concentration during calcium sulfate (c) precipitation in the stirred reactor were monitored in three solutions with 100, 70 and 60 mM of $CaSO_4$, depicted as 1, 2, and 3, respectively, and 0.5 M of NaCl that were prepared by mixing stock solutions with x and y in Eq. (1) equal to 0.15, 0.1; 0.18, 0.07; 0.19, 0.06, respectively. Relative changes of each of these characteristics, $\xi$, with time are plotted in FIG. 4; $\xi$=0 at the beginning and $\xi$=1 at the end of precipitation.

As can be seen in FIG. 4, the relative variations of these properties are similar, so that each of them can be used to characterize the degree of the solution supersaturation. As measurement of the electrical conductivity is easier to implement in a flow system, the degree of solution supersaturation in the RO unit can be evaluated by measuring its electrical conductivity in the unit inlet and outlet. The value of $\xi$ was then computed as the relative change of the solution conductivity in comparison with the total change, from about 54.2±1.5 to 46.8±1.3 mS/cm, recorded in the stirred reactor.

Precipitation from a supersaturated solution begins with the appearance of nuclei that, once formed, grow into larger particles. The induction periods of precipitation for these solutions taken as the time when $\xi$ underwent a sudden increase from zero in FIG. 4 are 20±2, 62±6 and 130±14 min. The concentrations $Ca^{2+}$ ions at the end of precipitation shown in FIG. 4 are 37.5±1.2, 36.6±0.7 and 36.2±0.4 mM, respectively. These measurements compare well with data on the equilibrium solubility of gypsum $CaSO_4 \cdot 2H_2O$ in aqueous solutions of NaCl [25-27]. The supersaturated solution is conventionally characterized by the supersaturation ratio $S_g$ that is considered with respect to the equilibrium between $Ca^{2+}$ and $SO_4^{2-}$ ions in the solution and in the gypsum crystal $$CaSO_4 \cdot 2H_2O \rightarrow Ca^{2+} + SO_4^{2-} + 2H_2O$$

so that $$S_g = a_{Ca^{2+}} a_{SO_4^{2-}} a_{H_2O}^2/(a_{Ca^{2+}} a_{SO_4^{2-}} a_{H_2O}^2)_{eq},$$

where $a_{Ca^{2+}}$, $a_{SO_4^{2-}}$ and $a_{H_2O}$ are respectively the activities of the calcium and sulfate ions and water with the ion activities $a_i$ expressed as the product of the activity coefficient ($\gamma_i$) and the molality ($m_i$ in mol/kg) of species i=$Ca^{2+}$, $SO_4^{2-}$ and the subscript "eq" indicates that these characteristics are taken at the equilibrium composition. Following [25], $S_g$ was calculated by taking the extended Debye-Hückel model that included adjustable parameters to account for the variation of the water activity with the solution ionic strength that yields $$S_g = m_{Ca^{2+}} m_{SO_4^{2-}} \gamma_{Ca^{2+}} \gamma_{SO_4^{2-}}/K_{sp}^0,$$

with $\log_{10}(\gamma_{Ca^{2+}}\gamma_{SO_4^{2-}}) = -(z_{Ca^{2+}}^2 + z_{SO_4^{2-}}^2)S\sqrt{I}/(1+A_{sp}\sqrt{I})-B'I+C'I^2$ and $2I = z_{Ca^{2+}}^2 m_{Ca^{2+}} + z_{SO_4^{2-}}^2 m_{SO_4^{2-}} + z_{Na^+} m_{Na^+} +$
$z_{Cl^-} m_{Cl^-},$ (3)

where I is the solution ionic strength in mol/kg, $K_{sp}^0$ is the solubility product constant for gypsum at zero ionic strength when $a_{H_2O}$ approaches unity, $z_i$ is the ion electrical charge, S is the Debye-Hückel coefficient, and $A_{sp}$, B', and C' are the adjustable parameters. The molal solubility of gypsum corresponds to $S_g=1$ with $m_{Ca^{2+}}=m_{SO_4^{2-}}$. The parameters in these expressions at 25° C. in mol/kg units are [25]: $\log_{10} K_{sp}^0=-4.374$, $S=0.509$, $A_{sp}=1.500$, $B'=0.0194$, $C'=0.0134$. The solubility of gypsum computed from Eq. (3) for 0.5M NaCl solution is 36.16 mM that agrees well with our measurements. The calculated values of $S_g$ for three supersaturated solutions in our experiments are respectively 5.92, 3.23, and 2.47.

In terms of the classical nucleation theory, the dependence of the induction time for nucleation of gypsum particles on the supersaturation ratio $S_g$ is given by [28]

$$\log_{10} t_{ind} = A + B/\log_{10}^2 S_g \text{ with } B = \beta\sigma^3 V_m^2 N_A f/v^2 (2.3RT)^3, \quad (4)$$

where A depends on frequencies with which ions $Ca^{2+}$ and $SO_4^{2-}$ in the solution attach and detach the gypsum nucleus and B represents a thermodynamic barrier to form a nucleus, $\beta$ is the shape factor equal to $16\pi/3$ for a spherical nucleus, $\sigma$ is the gypsum/solution interfacial energy, $V_m=74.44$ cm$^3$/g is the gypsum molar volume, $N_A$ is the Avogadro number, R is the gas constant, T is the absolute temperature, $v=2$ is the number of ions in which $CaSO_4 \cdot 2H_2O$ dissociates, and f is the factor that equals 1 for homogenous nucleation when a gypsum nucleus forms spontaneously in the solution and characterizes a decrease of interfacial energy for heterogeneous nucleation when it forms on the surface of a foreign solid particle. The slope of the straight line given by Eq. (4) can be used to evaluate the gypsum/solution interfacial energy [29]. The regime for values of $S_g$ greater than 2 is usually ascribed to homogenous nucleation with spherical nuclei. Using our data, we obtain $\sigma \sim 42$ mJ/m$^2$ for room temperature that lies within the range 8-44 mJ/m$^2$ of published data [30-38] and agrees well with the range 37-44 mJ/m$^2$ calculated from measurements in a stirred reactor [30-33].

Presented measurements demonstrate that $\xi$ computed from changes of the electrical conductivity, turbidity and $Ca^{2+}$ concentration advantageously provides a reliable parameter to characterize a supersaturated solution flowing through an RO unit.

b. Scale Formation in RO Unit

Formation of calcium sulfate scale on RO membranes was studied for a solution with 70 mM of $CaSO_4$ and 0.5M of NaCl. Experiments were carried out in the setup 10 depicted in FIG. 1 with and without the additional 100-ft coiled tubing 52 shown in FIG. 2. Two membranes were tested in every run. A membrane in RO unit 24 (FIG. 1) was exposed to the solution subjected to the magnetic field whereas the other in RO unit 26 (FIG. 1) was exposed to the solution not treated with the field. Runs were carried out with and without 100-ft coiled tubing 52 shown in FIG. 2. All membranes were washed after the test. The area of membrane 102 covered with scale deposits was calculated on the grid cells 104, see FIG. 3. Differences between data on electrical conductivity at the RO unit inlet of solutions flowing through the magnetic unit 16 and dummy unit 18, 56.1±0.6 mS/cm, and the initial solution conductivity, 54.2±1.5 mS/cm, were lying within the measurement errors that corresponded to $\xi=0$. The same value, 56.1±0.7 mS/cm, was found for the solution conductivity at the RO unit outlet in both branches of the setup without the 100-ft coiled tubing 52. When the 100-ft coiled tubing 52 was placed in both setup branches, the solution conductivity at the RO unit outlet was measured to be 53.9±0.8 mS/cm for all flow rates that yielded $\xi=0.14$.

The variation of the permeate flow rate with time for tested membranes was found to be well approximated as $$q(\text{g/min}) = -at^2 (\text{min}) + bt (\text{min}), \quad (5)$$

with the coefficient of determination $R^2>0.995$ for all tests. The first term in Eq. (5) with negative a describes a decrease in the permeate flow rate due to scale formation. Table 2, shown below, summarizes results of the statistical analysis of the mean and variance of coefficients in Eq. (5) obtained in both setup branches with and without the presence of 100-ft coiled tubing at different feed flow rates. Effects of these factors were analyzed for $\alpha=0.05$ corresponding to the confidence level of 95%.

TABLE 2

| All tested membranes | N | $\bar{a}$, g/min$^2$ | $S_a$, g/min$^2$ | $\bar{b}$, g/min | $S_b$, g/min |
|---|---|---|---|---|---|
| | 48 | 0.0221 | 0.0005 | 1.115 | 0.147 |

| Groups | $n_j$ | $\bar{a}_j$, g/min$^2$ | $S_{a_j}$, g/min$^2$ | $\bar{b}_j$, g/min | $S_{b_j}$, g/min |
|---|---|---|---|---|---|
| Effects of magnetic treatment | | | | | |
| j = 1, exposed to magnetic field | 24 | 0.0272 | 0.0005 | 1.123 | 0.159 |
| j = 2, not exposed to magnetic field | 24 | 0.0212 | 0.0002 | 1.107 | 0.142 |
| F-test | F | $F_\alpha$, $\alpha=0.05$ | | p | |
| Coefficient a | 1.56 | 4.05 | | 0.22 | |
| Coefficient b | 0.02 | 4.05 | | 0.89 | |
| Effects of additional 100-ft coiled tubing | | | | | |
| j = 1, without 100-ft coiled tubing | 16 | 0.0156 | 0.0003 | 1.047 | 0.184 |
| j = 2, with 100-ft coiled tubing | 32 | 0.0253 | 0.0005 | 1.149 | 0.130 |
| F-test | F | $F_\alpha$, $\alpha=0.05$ | | p | |
| Coefficient a | 2.22 | 4.05 | | 0.14 | |
| Coefficient b | 0.74 | 4.05 | | 0.39 | |
| Effects of feed flow rates | | | | | |
| j = 1, Q = 10 ml/min | 14 | 0.0416 | 0.0003 | 1.228 | 0.149 |
| j = 2, Q = 15 ml/min | 8 | 0.0250 | 0.0003 | 1.287 | 0.165 |
| j = 3, Q = 20 ml/min | 10 | 0.0154 | 0.0003 | 0.962 | 0.156 |
| j = 4, Q = 25 ml/min | 6 | 0.0163 | $4 \times 10^{-6}$ | 0.873 | 0.064 |
| F-test | F | $F_\alpha$, $\alpha=0.05$ | | p | |
| Coefficient a | 5.83 | 2.88 | | 0.003 | |
| Coefficient b | 2.35 | 2.88 | | 0.089 | |

As can be seen in Table 2, the influence of the magnetic treatment and the tubing length cannot be considered statistically significant as $F<F_{0.05}=4.05$ and $\alpha=0.05$ is smaller than the p-value. Also, the feed flow rate does not affect coefficient b in Eq. (5). However, its influence on coefficient a in Eq. (5) appears to be statistically significant as $F>F_{0.05}=2.88$ and $p=0.003$ is smaller than $\alpha=0.05$ (Table 2). Specifically, a decrease in the feed flow rate causes a to increase.

Scale deposits on membranes under our experimental conditions were formed directly by surface crystallization and by settling of particles precipitated in the bulk under the influence of gravity as the calcium sulfate density is about 2.3 g/cm$^3$. Gently dipping tested membranes in DI water ten times removed most of loosely adherent particles settled from the bulk. As an example, photos of not washed and washed membranes tested at the flow rate of 20 mL/min for 10 min in solutions flowing through the magnetic and dummy units are shown in FIGS. 5B and 5C, respectively.

The units were connected to the pump inlet through additional 100-ft tubing 52, see FIG. 2. The percentage of the membrane area covered with scale deposits was measured in each cell of the grid shown in FIG. 3. Variations of the scale coverage averaged over two cells in the perpendicular direction, along the flow path, are plotted in FIG. 5A, where the unfilled and filled symbols represent data for magnetic and dummy units, respectively, and the squares and circles represent data for not washed and washed membranes, respectively. Further, "L", in cm, is the distance the grid cells are located from the RO unit inlet. As can be the seen in FIG. 5 washing reduced the deposit coverage of the membranes by about 20%.

The percentage of the scale coverage averaged over the entire grid was used to evaluate effects of the magnetic treatment, the presence of 100-ft coiled tubing 52, and the feed flow rate on scale formation. Table 3, shown below, summarizes results of the statistical analysis of measurements in 48 runs each for about 15 min. The value $\alpha=0.05$ for the confidence level of 95% was also taken for comparison.

TABLE 3

| All tested membranes | N | $\overline{X}$, % | S, % |
|---|---|---|---|
| | 48 | 23.45 | 9.63 |
| Groups | $n_j$ | $\overline{X}_j$, % | $S_j$, % |
| Effects of magnetic treatment of solution | | | |
| j = 1, exposed to magnetic field | 24 | 24.81 | 8.34 |
| j = 2, not exposed to magnetic field | 24 | 22.09 | 10.78 |
| F-test | F | $F_\alpha$, $\alpha = 0.05$ | p |
| | 0.95 | 4.05 | 0.33 |
| Effects of additional 100-ft coiled tubing | | | |
| j = 1, without 100-ft coiled tubing | 16 | 21.54 | 4.71 |
| j = 2, with 100-ft coiled tubing | 32 | 24.40 | 11.28 |
| F-test | F | $F_\alpha$, $\alpha = 0.05$ | p |
| | 0.94 | 4.05 | 0.34 |
| Effects of feed flow rates | | | |
| j = 1, Q = 10 ml/min | 14 | 30.83 | 113.44 |
| j = 2, Q = 15 ml/min | 8 | 20.50 | 32.94 |
| j = 3, Q = 20 ml/min | 10 | 21.12 | 108.29 |
| j = 4, Q = 25 ml/min | 6 | 21.40 | 16.11 |
| F-test | F | $F_\alpha$, $\alpha = 0.05$ | p |
| | 3.53 | 2.88 | 0.025 |

As can be seen in Table 3, the variability between measurements in two branches of the flow setup is similar to the variability between data obtained in the setup with and without 100-ft coiled tubing at different flow rates. However, effects of both factors cannot be considered statistically significant as $F<F_{0.05}=4.05$ and the p-value is greater than $\alpha=0.05$. This result is illustrated by plots in FIGS. 6A and 6B which show that measurements of the percentage of the scale coverage with/without magnetic treatment 16 (FIG. 6A) and with/without the presence of 100-ft coiled tubing 52 (FIG. 6B) follow the Gaussian distribution, f(z), with the mean and variance taken from Table 3 for all tests:

$$f(z) = \frac{\exp(-z^2/2)}{S\sqrt{2\pi}} \text{ with } z = \frac{X - \overline{X}}{S} \quad (6)$$

On the other hand, the influence of the feed flow rate on scale formation appears to be statistically significant since $F>F_{0.05}=2.88$ and $p=0.025$ is smaller than $\alpha=0.05$ (Table 3).

The observation that reducing the feed flow rate intensifies scale formation, as Table 3 demonstrates, is consistent with data in Table 2 on increasing coefficient a in Eq. (5) with decreasing the feed flow rate. The facilitation of scale formation with decreasing the feed flow rate can be related to reducing the shear stress exerted on deposits crystallized on a membrane.

Figure 7A:
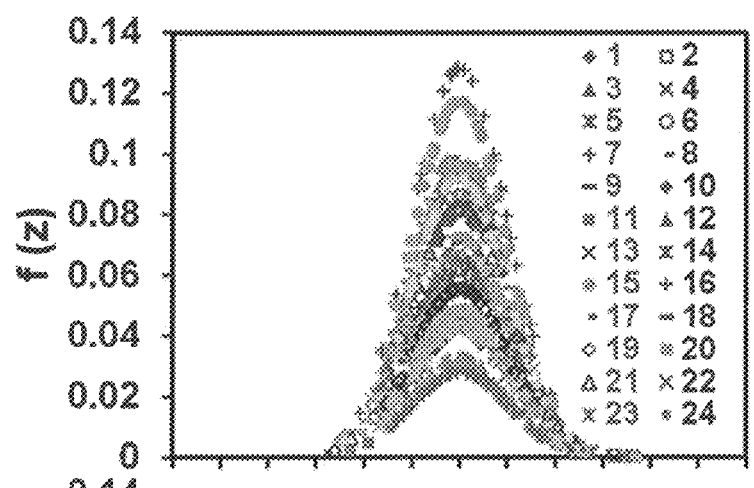
FIGS. 7A and 7B are plots showing scale coverage for solutions exposed and not exposed to a magnetic field according to the present disclosure.
Figure 7B:
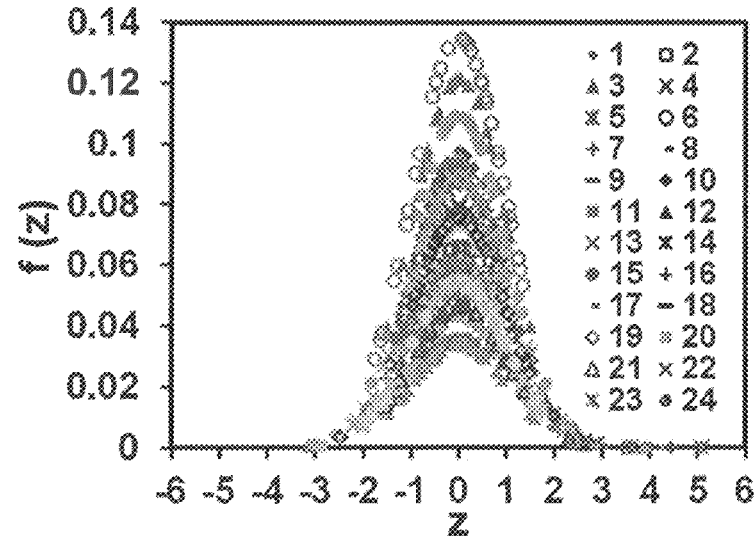

Plots presented in FIGS. 7A and 7B, depicting 24 membranes that were both exposed to and not exposed to a magnetic field, demonstrate that measurements of the percentage of the scale coverage of each grid cell on the membrane, being normalized with the mean and variance taken over the entire grid, follow the Gaussian distribution. Moreover, most measurements are falling within one standard deviation of the mean. These observations show clearly that scale formation was not affected by the distance of a particular location on the membrane surface from the RO unit inlet; therefore, that is consistent with the transient regime of crossflow filtration in step 2 of the proposed testing method. Contrary to conventional tests, this feature of our setup allows, for the first time, to control and measure the influence of the degree of solution supersaturation on the scale formation needed for prediction of the feed water treatment effectiveness for large industrial RO systems where the degree of solution supersaturation varies along the flow pathway.

Figures 8A, 8B, 8C, 8D, 8E, 8F:
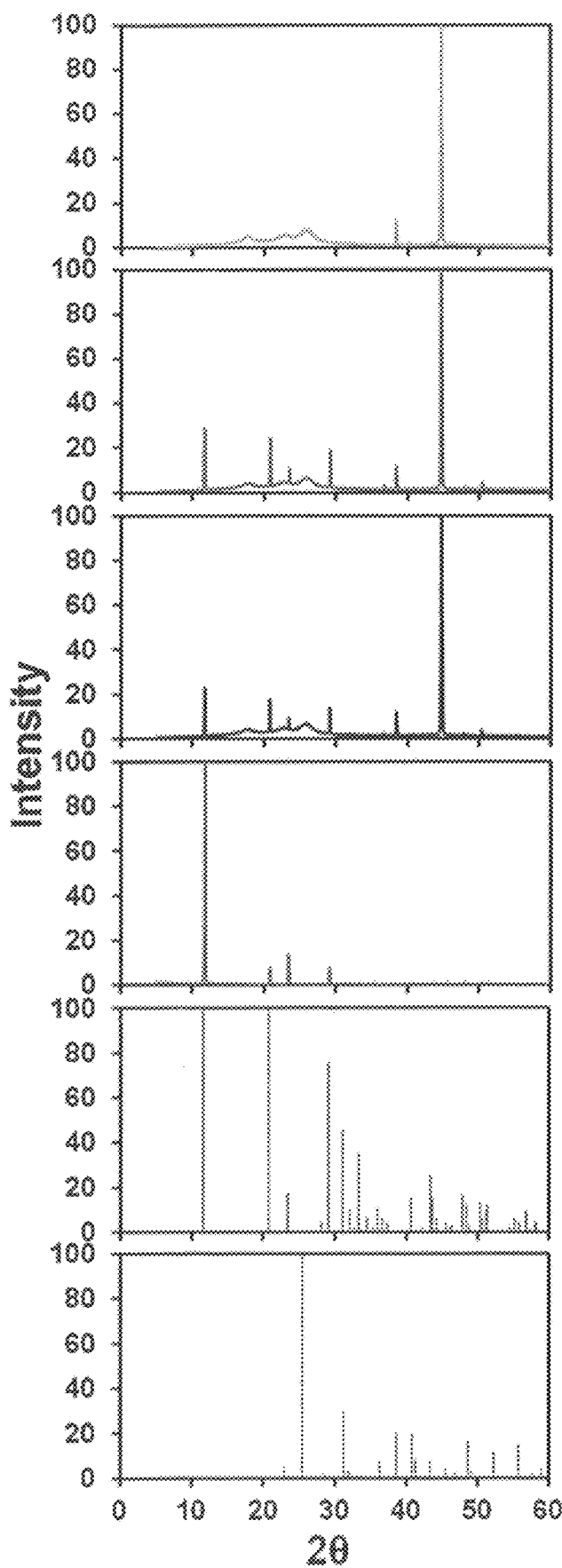
FIGS. 8A-8F are plots showing exemplary x-ray diffraction patterns according to the present disclosure.
Figure 9:
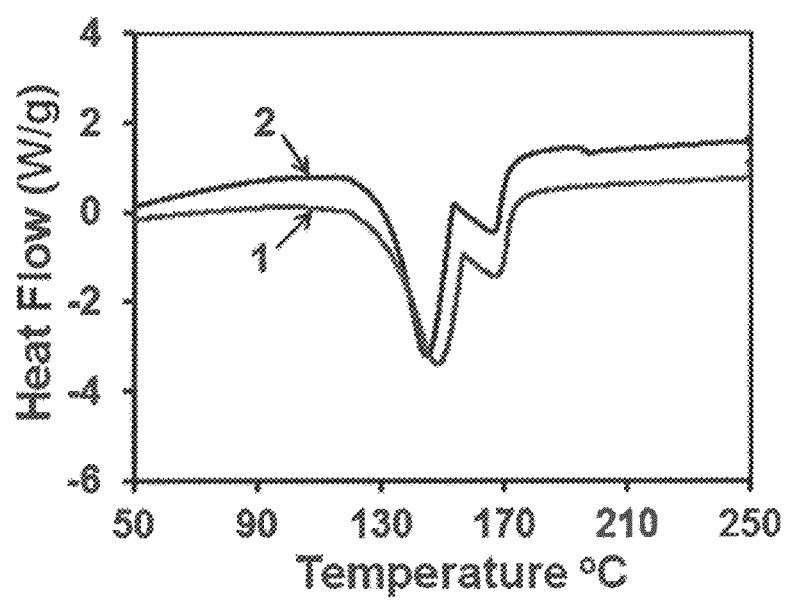
FIG. 9 is a plot showing an overlay of DSC curves according to the present disclosure.

X-Ray diffraction patterns obtained from washed membranes which were flow tested through a dummy unit (FIG. 8B) and a magnetic treatment unit (FIG. 8C) at the flowrate of 20 mL/min for 15 min. For comparison, diffraction patterns obtained from a fresh membrane (FIG. 8A) and particles precipitated from 70 mM $CaSO_4$/0.5 M NaCl solution in the stirred reactor (FIG. 8D) as well as patterns of dihydrate ($CaSO_4.2H_2O$) (FIG. 8E) and anhydrite ($CaSO_4$) (FIG. 8F) forms of calcium sulfate in the instrument library are also presented in FIG. 8. As can be seen in FIG. 8, diffraction patterns obtained from membranes in two branches of the flow setup are practically identical; the peaks in these patterns that differ from the peaks in the pattern obtained from a fresh membrane, FIG. 8A, can be attributed to scale deposits. Their locations and intensities are in good agreement with the peaks in the gypsum pattern in the instrument library, FIG. 8E. Peak locations in the diffraction pattern obtained from particles precipitated in the stirred reactor, FIG. 8D, correlate well with the gypsum pattern in the instrument library, but the peak intensities differ significantly. However, these particles can also be identified as gypsum because the peak intensities in the gypsum diffraction pattern are known to be determined by the texture that strongly depends on the conditions under which the gypsum is formed [39]. This conclusion is consistent with the DSC curves shown in FIG. 9 that were obtained from particles precipitated in the stirred reactor (1) and collected from scale deposits on membranes (2). Specifically, both curves demonstrate two similar endothermic peaks in 130-180° C. range that are related to the two-step process of gypsum dehydration [40, 41].

Figure 10A:
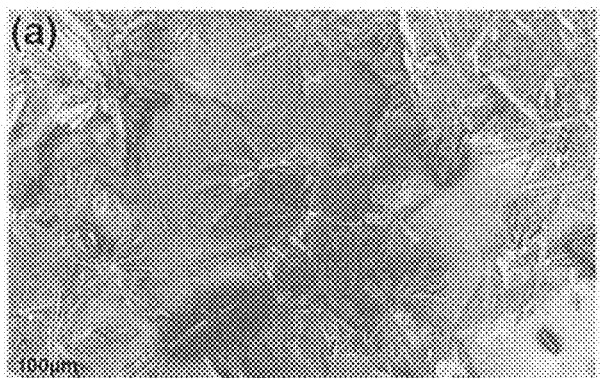
FIGS. 10A-10D are images related to rosette structures of scale deposits.
Figure 10B:
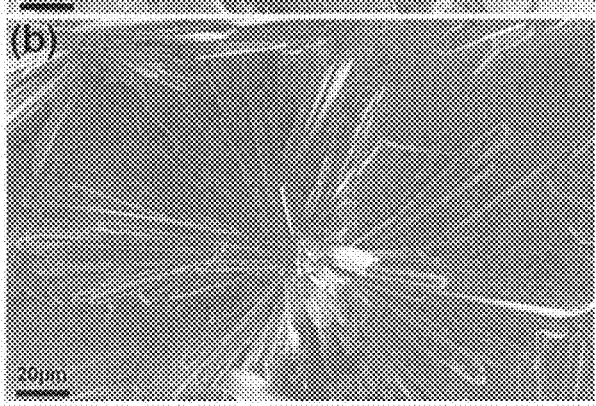
Figure 10C:
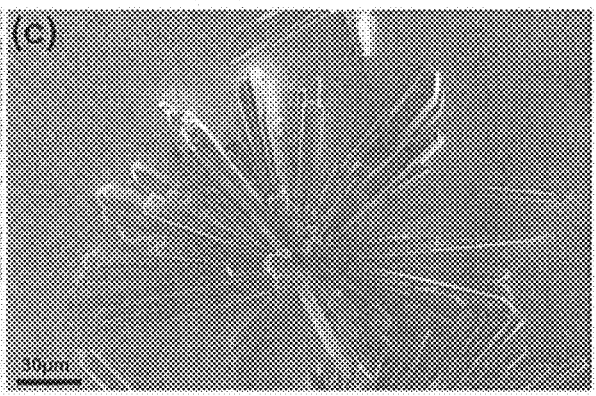
Figure 10D:
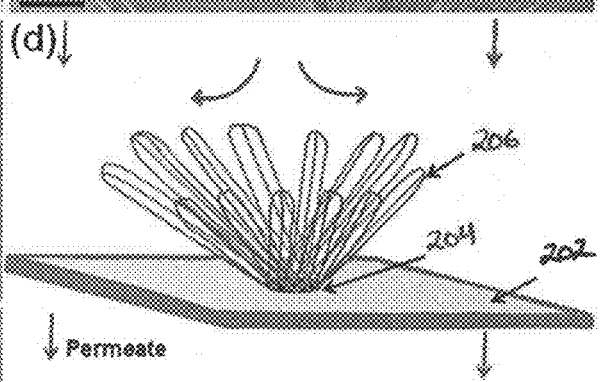

Scale deposits formed on the membrane surface, exposed to the flow of 70 mM $CaSO_4$/0.5 M NaCl solution at a flowrate of 20 mL/min for 15 min, exhibit a rosette structure formed by needle-like crystals growing radially from a single growth center crystallized on the membrane surface, see FIGS. 10A-10C. It is similar to the morphology of gypsum deposits on RO membranes observed in experiments [42-44] which were conducted at low supersaturation of the feed solution. Accordingly, crystals were found to grow in the direction opposite to the feed flow and the well-developed rosette morphology appeared only at the channel exit. In our experiments carried out at high supersaturation of the feed solution, rosette structures formed all over the membrane surface (FIG. 5). This fact taken together with observations for RO [42-44] and nanofiltration [45] membranes indicates that the formation of gypsum rosette structures requires a sufficiently high solution supersaturation and is controlled by the precipitation kinetics in the vicinity of the membrane surface. The schematic in FIG. 10D illustrates the growth of rosette structures on membrane surface 202. Depicting needle crystals 206 growing from gypsum surface nucleus 204 and arrows showing the flow towards membrane surface 202.

4. Summary

The present disclosure provides advantageous methods, devices and systems for quick (10-30 min) benchtop tests of the effectiveness of magnetic treatment of feed water for reducing mineral scaling on a RO membrane. The procedure of conducting testing in step 2 in the transient regime of crossflow filtration in an RO unit was validated by experiments on an aqueous $CaSO_4$/NaCl solution at a controlled level of supersaturation with $CaSO_4$. The feed solution was formed by mixing $CaCl_2$/NaCl and $Na_2SO_4$/NaCl solutions. To quantify its supersaturation in step 1, variations of the electrical conductivity, turbidity, and $Ca^{2+}$ concentration during gypsum precipitation from the solution were studied in the stirred reactor. As relative changes of these properties were found to be similar, measuring the solution electrical conductivity was chosen to characterize the supersaturation level in the flow system. To improve the test resolution, the flow setup includes two similar branches, both equipped with an RO unit and a pump. The branches were operated in parallel at the same flow rate and transmembrane pressure and fed with a solution at the same level of supersaturation, but the feed was exposed to a magnetic field only in one of them. The proposed methodology allows, for the first time, the detailed study of the scale formation under a controlled high degree supersaturation of the feed solution that is typical of industrial RO systems.

Effects of the magnetic treatment of the feed solution and the level of its supersaturation on gypsum scaling under the disclosed experimental conditions were found to be statistically insignificant. While similar results were reported in the literature, many publications demonstrated that magnetic treatment facilitated reduction of scale formation, depending on particular physicochemical conditions. Therefore, the presented experimental data should not be considered as negating the promise of the treatment of feed water with a magnetic field in specific applications.

The purpose of the disclosed methodology is to help evaluate in benchtop tests whether a particular magnetic water conditioner may be useful under specific operating conditions of a large industrial RO system. The approach is to measure the water electrical conductivity, or other parameters characterizing the variation of the degree of solution supersaturation, along the flow path through the RO system of interest and find the range of its supersaturation by comparing these measurements with data on the variation of the feed electrical conductivity, or other parameters changing in the course of precipitation in a stirred reactor, in step 1. The particular magnetic water conditioner would be successful only if benchtop tests reveal its efficiency over the range of supersaturation, flow rate and transmembrane pressure observed in the system of interest. The proposed methodology can also be useful for evaluating the efficiency of other technologies for water treatment in flow systems, even for testing the efficacy of specific antiscalant additives.

Although the present disclosure describes the disclosed methods and apparatus/systems with reference to exemplary embodiments thereof, the present disclosure is not limited by or to such exemplary embodiments. Rather, the present disclosure may be modified, altered or otherwise varied without departing from the spirit or scope of the present invention.

REFERENCES

1. M.A. Shannon, P.W. Bohn, M. Elimelech, J.G. Georgiadis, B.J. Marinas, A.M. Mayes, Science and technology for water purification in the coming decades, Nature 452 (2008) 301-310.
2. M. Elimelech, W.A. Phillip, The future of seawater desalination: Energy, technology, and the environment, Science 333 (2011) 712-717
3. L. Malaeb, G.M. Ayoub, Reverse osmosis technology for water treatment: State of the art review, Desalination 267 (2011) 1-8.
4. S.S. Shenvi, A.M. Isloora, A.F. Ismail, A review on RO membrane technology: Developments and challenges, Desalination 368 (2015) 10-26.
5. J.S. Baker, S.J. Judd, Magnetic amelioration of scale formation (review), Water Res. 30 (1996) 247-260,
6. Ritu D. Ambashtaa, Mika Sillanpää, Water purification using magnetic assistance: A review, J. Hazard. Mater. 180 (2010) 38-49
7. N.S. Zaidi, J. Sohaili, K. Muda, M., Sillanpää, Magnetic field application and its potential in water and wastewater treatment systems, Sep. Purif. Rev. 43 (2014) 206-240.
8. H. Al-Qahtani, Effect of magnetic treatment on Gulf seawater, Desalination 107 (1996) 75-81.
9. C.V. Vedavyasan, Potential use of magnetic fields a perspective, Desalination 134 (2001) 105-108.
10. J.S. Baker, S.J. Judd, S.A. Parsons, Antiscale magnetic pretreatment of reverse osmosis feedwater, Desalination 110 (1997) 151-166.
11. A.D. Kney, S.A. Parsons, A spectrophotometer-based study of magnetic water treatment: Assessment of ionic vs. surface mechanisms, Water Res. 40 (2006) 517-524.
12. J. Li, J. Liu, T. Yang, C. Xiao, Quantitative study of the effect of electromagnetic field on scale deposition on nanofiltration membranes via UTDR, Water Res. 41 (2007) 4595-4610.
13. M. Gryta, The influence of magnetic water treatment on $CaCO_3$ scale formation in membrane distillation process, Sep. Purif. Technol. 80 (2011) 293-299.
14. R. Vardanega, M.V. Tres, M.A. Mazutti, H. Treichel, D. De Oliveira, M., Di Luccio, J.V. Oliveira, Effect of magnetic field on the ultrafiltration of bovine serum albumin, Bioprocess Biosyst. Eng. 36 (2013) 1087-1093.
15. I.Otsuka, S. Ozeki, Does magnetic treatment of water change its properties? J. Phys. Chem. B 110 (2006) 1509-1512.
16. P. Vallee, J. Lafait, L. Legrand, P. Mentré, M.-O. Monod, Y. Thomas, Effects of pulsed low-frequency electromagnetic fields on water characterized by light scattering techniques: Role of bubbles, Langmuir 21 (2005) 2293-2299.
17. B. Stuyven, G. Vanbutsele, J. Nuyens, J. Vermant, J.A. Martens, Natural suspended particle fragmentation in magnetic scale prevention device, Chem. Eng. Sci. 64 (2009) 1904-1906.

18. M. Colic, D. Morse, The elusive mechanism of the magnetic 'memory' of water, Colloid Surface A 154 (1999) 167-174.
19. L. Holysz, A. Szczes, E. Chibowski, Effects of a static magnetic field on water and electrolyte solutions, J. Colloid Interface Sci. 316 (2007) 996-1002.
20. A.Szcze, E. Chibowski, L. Hozysz, P. Rafalski, Effects of static magnetic field on electrolyte solutions under kinetic condition, J. Phys. Chem. A 115 (2011) 5449-5452.
21. M. Mulder, Basic Principles of Membrane Technology. Kluwer Academic Publishers, Dordrecht, NL, 1991.
22. J.W. Mullin, Crystallization, 4th Ed., Elsevier, 2001.
23. S. Vashisth, V., Kumar, K.D.P., Nigam, A review on the potential applications of curved geometries in process industry, Ind. Eng. Chem. Res. 47 (2008) 3291-3337.
24. B.C. Gupta, I. Guttman, Statistics and Probability with Applications for Engineers and Scientists, John Wiley & Sons, 2013.
25. W.L. Marshall, R. Slusher, Thermodynamics of calcium sulfate dihydrate in aqueous sodium chloride solutions, 0-110°, J. Phys. Chem. 70(12) (1966) 4015-4027.
26. K.U.G. Raju, G. Atkinson, The thermodynamics of "scale" mineral solubilities. 3. Calcium sulfate in aqueous NaCl, J. Chem. Eng. Data 35 (1990) 361-367.
27. R. Sheikholeslami, H.W.K. Ong, Kinetics and thermodynamics of calcium carbonate and calcium sulfate at salinities up to 1.5 M, Desalination 157 (2003) 217-234.
28. O. Sohnel, J.W. Mullin, Interpretation of crystallization induction periods, J. Colloid Interface Sci. 123 (1988) 43-50.
29. W. Wu, G.H. Nancollas, Determination of interfacial tension from crystallization and dissolution data: a comparison with other methods. Adv. Colloid Interface Sci. 79 (1999) 229-279.
30. S. He, J.E. Oddo, M.B. Tomson, The seeded growth of calcium sulfate dehydrate crystals in NaCl solutions up to 6 m and 90° C., J. Colloid Interface Sci. 163 (1994) 372-378.
31. A.Lancia, D. Musmarra, M. Prisciandaro, Measuring induction period for calcium sulfate dihydrate precipitation, AIChE J. 45(2) (1999) 390-397.
32. M. Prisciandaro, A. Lancia, D. Musmarra, Gypsum nucleation into sodium chloride solutions, AIChE J. 47(4) (2001) 929-934
33. M. Prisciandaro, A. Lancia, D. Musmarra, The retarding effect of citric acid on calcium sulfate nucleation kinetics, Ind. Eng. Chem. Res. 42 (2003) 6647-6652.
34. P.G. Klepetsanis, E. Dalas, P.G. Koutsoukos, Role of temperature in the spontaneous precipitation of calcium sulfate dehydrate, Langmuir 15 (1999) 1534-1540.
35. D. Hasson, A. Drak, R. Semiat, Induction times induced in an RO system by antiscalants delaying $CaSO_4$ precipitation, Desalination 157 (1-3) (2003) 193-207.
36. F. Alimi, H. Elfil, A. Gadrib, Kinetics of the precipitation of calcium sulfate dehydrate in a desalination unit, Desalination 157 (2003) 9-16.
37. A.Hina, G.H. Nancollas, M. Grynpas, Surface induced constant composition crystal growth kinetics studies, The brushite-gypsum system. J. Cryst. Growth 223 (2001) 213-224.
38. M.H.H. Mahmoud, M.M. Rashad, I.A. Ibrahim, E.A. Abdel-Aal, Crystal modification of calcium sulfate dihydrate in the presence of some surface-active agents. J. Colloid Interface Sci. 270 (2004) 99-105
39. S. Follner, A. Wolter, K. Helming, C. Silber, H. Bartels, H. Follner, On the real structure of gypsum crystals, Cryst. Res. Technol. 37 (2-3) (2002) 207-218.
40. D. Fatu, Kinetics of gypsum dehydration, J. Therm. Anal. Calorim. 65 (2001) 213-220.
41. J. Lopez-Beceiro, C. Gracia-Fernandez, J. Tarrio-Saavedra, S. Gomez-Barreiro, R. Artiaga, Study of gypsum by PDSC, J. Therm. Anal. Calorim. 109 (2012) 1177-1183.
42. W.-Y. Shih, A. Rahardianto, R.-W. Lee, Y. Cohen, Morphometric characterization of calcium sulfate dihydrate (gypsum) scale on reverse osmosis membranes. J. Memb. Sci. 252 (2005) 253-263.
43. A.Rahardianto, W.-Y. Shih, R.-W. Lee, Y. Cohen, Diagnostic characterization of gypsum scale formation and control in RO membrane desalination of brackish water. J. Memb. Sci. 279 (2006) 655-668.
44. M. Uchymiak, E. Lyster, J. Glater, Y. Cohen, Kinetics of gypsum crystal growth on a reverse osmosis membrane, J. Memb. Sci. 314 (2008) 163-172.
45. S. Lee, C.-H. Lee, Effect of operating conditions on $CaSO_4$ scale formation mechanism in nanofiltration for water softening, Water Res. 34 (2000) 3854-3866.

The invention claimed is:
1. A method for benchtop evaluation of effectiveness of a water treatment modality, comprising:
   a. providing a benchtop reverse osmosis (RO) system including RO membranes that operate in a transient regime of crossflow filtration for treated and untreated feed water,
   b. measuring kinetics of precipitation of a supersaturated solution in a stirred reactor based on at least one feed characteristic; and
   c. characterizing the solution supersaturation based on the at least one solution characteristic during a certain period of time and a total relative change of the characteristic at a beginning and an end of the precipitation process;
   wherein flow through the RO system is a single-pass flow, and
   wherein the testing is performed using a flow setup that includes two similar branches, both equipped with an RO membrane and a pump that are operating in the transient regime at the same flow rate and transmembrane pressure and fed with a solution at the same level of supersaturation measured in the stirred reactor, wherein only one branch exposes the feed to a magnetic field.

2. The method of claim 1, wherein the feed characteristic is selected from a group consisting of electrical conductivity, turbidity, and concentrations of ions of sparingly soluble salts.

3. The method of claim 1, wherein at least one of polarized microscopy with image processing software, scanning electron microscopy (SEM), X-ray diffractometry (XRD), and differential scanning calorimetry (DSC) is used to characterize the scale formed on the RO membrane.

4. The method of claim 1, wherein the evaluation is completed within a period of between about 10 minutes and 30 minutes.

5. A method for benchtop evaluation of effectiveness of a water treatment modality, comprising:
   a. providing a benchtop reverse osmosis (RO) system including RO membranes that operate in a transient regime of crossflow filtration for treated and untreated feed water, b. measuring kinetics of precipitation of a supersaturated solution in a stirred reactor based on at least one feed characteristic; and c. characterizing the solution supersaturation in the benchtop reverse osmosis (RO) system based on the at least one solution characteristic during a certain period of time and a total relative change of the characteristic at a beginning and an end of the precipitation process;

wherein flow through the RO system is a single-pass flow, and wherein the characterizing step includes characterization of solution supersaturation based at least in part on a parameter $\xi(t)$ that is calculated as the ratio between a change in one of said feed characteristics during a period of time t and the total change so that $\xi=0$ and $\xi=1$ are at the beginning and the end of the precipitation process, respectively.

6. An apparatus for evaluating effectiveness of a water treatment modality, comprising:

a. a benchtop reverse osmosis (RO) system that includes RO membranes that operate in a transient regime of crossflow filtration for treated and untreated feed water, wherein flow through the RO system is a single-pass flow;

b. means associated with the benchtop RO system for measuring kinetics of precipitation of a supersaturated solution in a stirred reactor based on at least one feed characteristic; and c. means associated with the benchtop RO system for characterizing the solution supersaturation based on the at least one solution characteristic during a certain period of time and a total relative change of the characteristic at a beginning and an end of the precipitation process;

wherein the testing is performed using a flow setup that includes two similar branches, both equipped with an RO membrane and a pump that are operating in the transient regime at the same flow rate and transmembrane pressure and fed with a solution at the same level of supersaturation measured in the stirred reactor, wherein only one branch exposes the feed to a magnetic field.

7. The apparatus of claim 6, wherein the feed characteristic is selected from a group consisting of electrical conductivity, turbidity, and concentrations of ions of sparingly soluble salts.

8. The apparatus of claim 6, wherein at least one of polarized microscopy with image processing software, scanning electron microscopy (SEM), X-ray diffractometry (XRD), and differential scanning calorimetry (DSC) is used to characterize the scale formed on the RO membrane.

9. The apparatus of claim 6, wherein the evaluation is completed within a period of between about 10 minutes and 30 minutes.

10. An apparatus for evaluating effectiveness of a water treatment modality, comprising:

a. a benchtop reverse osmosis (RO) system that includes RO membranes that operate in a transient regime of crossflow filtration for treated and untreated feed water, wherein flow through the RO system is a single-pass flow;

b. means associated with the benchtop RO system for measuring kinetics of precipitation of a supersaturated solution in a stirred reactor based on at least one feed characteristic; and c. means associated with the benchtop RO system for characterizing the solution supersaturation based on the at least one solution characteristic during a certain period of time and a total relative change of the characteristic at a beginning and an end of the precipitation process;

wherein the characterizing step includes characterization of solution supersaturation based at least in part on a parameter $\xi(t)$ that is calculated as the ratio between a change in one of said feed characteristics during a period of time t and the total change so that $\xi=0$ and $\xi=1$ are at the beginning and the end of the precipitation process, respectively.

* * * * *